(12) United States Patent
Joshi et al.

(10) Patent No.: US 9,387,178 B2
(45) Date of Patent: *Jul. 12, 2016

(54) MODIFIED RELEASE TRANEXAMIC ACID FORMULATION

(71) Applicant: Actavis, Inc., Parsippany, NJ (US)

(72) Inventors: Mayank R. Joshi, Weston, FL (US); Shahin Fesharaki, Weston, FL (US)

(73) Assignee: Actavis, Inc., Parsippany, NJ (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/083,563

(22) Filed: Nov. 19, 2013

(65) Prior Publication Data

US 2014/0079779 A1 Mar. 20, 2014

Related U.S. Application Data

(63) Continuation of application No. 12/956,036, filed on Nov. 30, 2010, now Pat. No. 8,597,683.

(51) Int. Cl.
*A61K 9/20* (2006.01)
*A61K 31/195* (2006.01)
*A61P 7/04* (2006.01)
*A61K 9/28* (2006.01)

(52) U.S. Cl.
CPC ............ *A61K 9/2846* (2013.01); *A61K 9/2054* (2013.01); *A61K 9/2077* (2013.01); *A61K 31/195* (2013.01)

(58) Field of Classification Search
None
See application file for complete search history.

(56) References Cited

U.S. PATENT DOCUMENTS

| | | | |
|---|---|---|---|
| 4,465,662 A | 8/1984 | Sato et al. | |
| 5,506,264 A | 4/1996 | Fujimura et al. | |
| 7,351,740 B2 | 4/2008 | Zerangue et al. | |
| 7,947,739 B2 | 5/2011 | Moore et al. | |
| 2003/0133985 A1 | 7/2003 | Louie-Helm et al. | |
| 2004/0052843 A1 | 3/2004 | Lerner et al. | |
| 2005/0025825 A1 | 2/2005 | Heasley et al. | |
| 2005/0090473 A1* | 4/2005 | Devane et al. | 514/150 |
| 2005/0202086 A1* | 9/2005 | Jureczek | 424/468 |
| 2005/0244495 A1 | 11/2005 | Moore et al. | |
| 2005/0245614 A1 | 11/2005 | Moore et al. | |
| 2006/0024365 A1 | 2/2006 | Vaya et al. | |
| 2006/0127476 A1 | 6/2006 | Heasley et al. | |
| 2008/0206350 A1 | 8/2008 | Gryczke | |
| 2008/0280981 A1 | 11/2008 | Moore et al. | |
| 2009/0017114 A1 | 1/2009 | Heasley et al. | |
| 2009/0048341 A1 | 2/2009 | More et al. | |
| 2009/0209646 A1 | 8/2009 | Moore et al. | |
| 2009/0214644 A1 | 8/2009 | Heasley et al. | |
| 2009/0215898 A1 | 8/2009 | Heasley et al. | |
| 2009/0258067 A1* | 10/2009 | Zhou et al. | 424/472 |
| 2010/0143468 A1 | 6/2010 | Moore et al. | |

FOREIGN PATENT DOCUMENTS

| | | |
|---|---|---|
| EP | 1586315 | 10/2005 |
| JP | 2007070142 | 3/2007 |
| WO | 2008114506 | 9/2008 |

OTHER PUBLICATIONS

Lee, Sun Hwa, International Search Report for PCT/US2011/061794, dated Jun. 8, 2012, Korean Intellectual Property Office, Government Complex-Daejeon, 189 Cheongsa-ro, Seo-gu, Daejeon, 302-701, Republic of Korea.
Lee, Sun Hwa, Written Opinion of the International Searching Authority for PCT/US2011/061794, dated Jun. 8, 2012, Korean Intellectual Property Office, Government Complex-Daejeon, 189 Cheongsa-ro, Seo-gu, Daejeon, 302-701, Republic of Korea.
Lysteda Package Insert, tranexamic acid tablets, Xanodyne Pharmaceuticals, Inc., Nov. 2009.
Methocel Cellulose Ethers in Aqueous Systems for Tablet Coating, DOW, Jul. 2002.
Copovidone, Summary of the USP-NF draft monograph "Copovidone" published in US Pharmacopoeial Forum, vol. 24., No. 4, p. 6456 to 6459, BASF ExAct, p. 4, No. 3, Nov. 1999.
Methocel, General Properties of Methocel, Premium Cellulose Ethers, COLORCON, 2009.

* cited by examiner

*Primary Examiner* — Tracy Vivlemore
*Assistant Examiner* — Monica Shin
(74) *Attorney, Agent, or Firm* — Florek & Endres, PLLC

(57) ABSTRACT

A modified release dosage form for the oral administration of tranexamic acid.

24 Claims, No Drawings

MODIFIED RELEASE TRANEXAMIC ACID FORMULATION

BACKGROUND OF THE INVENTION

The present invention relates to a stable formulation of tranexamic acid that provides improved taste profile and a therapeutic administration of tranexamic acid.

Tranexamic acid (trans-4-aminomethyl-cyclohexanecarboxylic acid) is an antifibrinolytic agent, which is used to prevent lysis or dissolution of fibrin clots. Its mechanism of action is as a competitive inhibitor of plasminogen activation, and as a noncompetitive inhibitor of plasmin; both plasminogen and plasmin are activators of fibrinolysis and active clot-lysing agents. Tranexamic acid assists in stabilizing fibrin clots, which maintains coagulation and assists in the control of bleeding.

Tranexamic acid is commercially available as 650 mg oral tablets under the trade name LYSTEDA® from Ferring Pharmaceuticals. Tranexamic acid is also available in intravenous form under the trade name CYKLOKAPRON® from Pharmacia and Upjohn.

Tranexamic acid is used to control excess bleeding, such as heavy bleeding during menstruation (menorrhagia). Women that suffer from menorrhagia are typically treated orally with 500 mg tranexamic acid tablets, which are administered three or four times daily. The total daily dosage ranges from 3 grams/day (two tablets every eight hours) to 6 grams/day (three tablets every six hours). Unfortunately, this treatment can cause adverse gastrointestinal reactions, including nausea, vomiting, diarrhea, and cramping. It is believed these gastrointestinal side effects are due to either large dosages of tranexamic acid and/or a rapid rate of release of tranexamic acid into the stomach following administration.

Additionally tranexamic acid has a bitter taste, and prior art tranexamic acid dosage forms are reported to be difficult to consume. This results in poor patient compliance.

A further disadvantage of such tranexamic acid-containing oral dosage forms is that they are unstable and tend to discolor upon aging. Prior art formulations are known which use cyclodextrin, chelating agents or a polycarboxylic acid derivative to prevent discoloration and improve stability. However, these approaches have several drawbacks, including lack of complete taste-masking and reduced stability of the tranexamic acid.

Other proposed attempts to solve the taste and stability problems have used enteric or delayed release coatings that delay the release of the tranexamic acid until after it has passed through the low pH environment of the stomach. These delayed release formulations were developed to improve the stability of the tranexamic acid dosage form, as well as improve patient compliance due to the poor taste profile of tranexamic acid. These techniques are described in U.S. Published Application Nos. 2005/0244495; 2005/0245614 and 2005/0025825. These delayed and modified release formulations employ dual layer coating techniques that involve the application of a separate functional coating and a seal coating layer, an operation which increases the length of the manufacturing process and the cost of the product. Further, enteric coated dosage forms can result in an unnecessarily long delay in the release of the tranexamic acid, thereby decreasing the effectiveness of the tranexamic acid.

The applicants have surprisingly discovered that the combination of a controlled release core and a coating system that avoids the need to use additional coating layers, or enteric coating agents on the tranexamic acid core tablet can produce stable, therapeutic and taste-masked solid dosage forms.

SUMMARY OF THE INVENTION

The present invention provides a novel dosage form of tranexamic acid that comprises or consists essentially of:
(a) a core comprising or consisting essentially of tranexamic acid and a release controlling material; and
(b) a coating layer on said core that comprises or consists essentially of a coating agent which is insoluble in water, but soluble in aqueous media with a pH below 5 and preferably a pH below 4.

The core may be in the form of pellets, mini tablets or compressed tablet cores. As used herein the term "pellets" refer to spherical or irregularly shaped particles having an average diameter of less than 1 mm. As used herein the terms "mini tablet" or "minitabs" are used interchangeably and refer to solid dosage forms that have a length and/or width that ranges from 1 mm or greater to about 5 mm. As used herein the term "tablet" is used in its conventional manner, and generally refers to a solid dosage form with a length and/or width greater than 5 mm. In the case of mini tablets and tablets the core is preferably a homogenous or uniform mixture of ingredients, i.e., not a multilayer core. The core may further comprise conventional tableting excipients such as binders, fillers, disintegrants, glidants, lubricants or mixtures thereof.

The coating layer is applied to and surrounds the core. In one embodiment of the present invention, the dosage forms employs only one functional coating layer and may optionally further comprise aesthetic coatings such as rapidly dissolving color coatings or wax polishing coatings. The aesthetic coatings, if employed, will not affect the release characteristics of the tranexamic acid from the dosage form. In addition to the coating agent, which is insoluble in water but soluble in aqueous media with a pH below 4, the coating layer, also referred to herein as a "functional coating," may further comprise conventional processing aids such as binders, fillers, pigments, lubricants, plasticizers and mixtures thereof.

The coating agent, which is insoluble in water but soluble in aqueous media with a pH below 5, preferably a pH below 4, may be an amino methacrylate copolymer, preferably an aminoalkyl methacrylate copolymer. An example of a coating agent that is insoluble in water but soluble in aqueous media with a pH below 4, more preferably below 3, is commercially available from Degussa under the trade name EUDRAGIT® E.

Accordingly, it is a primary object of this invention to provide a solid oral pharmaceutical dosage formulation of tranexamic acid that is stable upon prolonged storage, is stable when administered to a patient and is capable of providing the desired therapeutic effect.

These and other objects of the invention will become apparent from a review of the present specification.

DETAILED DESCRIPTION OF THE INVENTION

The tranexamic acid formulation of the invention may be prepared by mixing the tranexamic acid with the release controlling material, and optionally conventional processing aids, such as binders, fillers, disintegrants, glidants, lubricants, or mixtures thereof. The mixture may be directly compressed into a tablet or mini tablet core or granulated, either by wet or dry techniques to prepare pellet cores. The granules may also be used to prepare compressed tablet or mini tablet cores.

The tranexamic acid present in the core may comprise from about 40 to 95 wt %, preferably about 50 to 90 wt %, and most preferably about 55-85 wt % of the core.

Release controlling materials employed in the core may be hydrophilic and/or hydrophobic materials such as gums, cellulose ethers, acrylic resins, waxes, protein derived materials, or polyethylene oxides. Additional examples of release controlling materials that may be used in the present invention include hydrogenated castor oil, hydrogenated vegetable oils, natural and synthetic waxes such as beeswax, glycowax, castor wax, glycerol monostearate, glyceryl behenate, stearyl alcohol, alginates, carrageenan, carbomers, xanthan gum, locust bean gum, hydroxypropyl methylcelluloses, hydroxypropyl celluloses, hydroxyethyl celluloses, carboxymethycelluloses, polyethylene oxides and mixtures of thereof.

One embodiment of the present invention employs hydrophilic release controlling polymers as the release controlling material, and preferably water soluble release controlling polymers that swell and or gel when exposed to aqueous mediums. Some examples of the hydrophilic release controlling polymers include, but are not limited to hydroxypropyl methylcelluloses, hydroxypropyl celluloses, hydroxyethyl celluloses, carboxymethycelluloses, polyethylene oxides, and mixtures thereof. Representative examples of hydrophilic release controlling polymers are low viscosity hypromellose (such as METHOCEL® E 5 Premium, which is commercially available from Dow Chemical) and high molecular weight polyethylene oxides (such as POLYOX WSR 301, WSR 303 or WSR COAGULANT). The release controlling polymer is present in the present invention at approximately 1 to 25 wt %, preferably about 2 to 20 wt % and most preferably about 3 to 15 wt %.

Binders that may be employed in the core of the present invention are preferably a water soluble polymer of the group consisting of polyvinyl alcohol, polyvinylpyrrolidone, methylcellulose, hydroxypropyl cellulose, hydroxymethyl cellulose, copovidone (a/k/a copolymer of 1-vinyl-2-pyrrolidone and vinyl acetate) and mixtures thereof. A water soluble binder is preferred, which is applied from an organic medium such as ethanol at a level of from about 0.1 to 10 wt % and preferably from about 1 to 5 wt % of binder based on the total weight of the granulation. The preferred binder is copovidone. The binders typically exhibit a lower molecular weight than the release controlling materials.

Fillers that may be used in the core of the present invention include, but are not limited to sugars such as lactose, dextrose, sucrose, maltose, mannitol, microcrystalline cellulose and mixtures thereof. The filler may comprise from about 5 to 50 wt % and preferably about 10 to 30 wt % based on the total weight of the core.

Disintegrants that may be used in the core of the present invention include corn starch, potato starch, croscarmellose sodium, crospovidone, sodium starch glycolate, and mixtures thereof. The disintegrant may be present in the core from about 0.1 to 10 wt % and preferably about 0.5 to 5 wt % based on the total weight of the core.

The core may also comprise a flow aid or glidant. A glidant is an excipient that improves the flow characteristics of a compressible powder such as tablet ingredients or granules. Two of the most common glidants are colloidal silicon dioxide (CAB-O-SIL®) and Quso (also known as Phila Quartz). The amount of glidant that can be used in the present invention ranges from about 0.01 to 5 wt % and preferably about 0.1 to 2 wt % based on the total weight of the core. The preferred glidant is colloidal silicon dioxide.

Suitable lubricants possess anti-sticking or anti-tacking properties. Suitable lubricants used in preparing solid dosage forms may include talc, stearic acid, magnesium stearate, glyceryl monostearate, sodium stearyl fumarate, glyceryl behenate, hydrogenated oils, polyethylene glycols and sodium stearate. The amount of lubricant that can be used in the present invention ranges from about 0.01 to 10 wt % and preferably about 0.5 to 5 wt % based on the total weight of the core.

Once the core is prepared it is coated with a functional coating or a coating layer that comprises or consists essentially of a coating agent that is insoluble in water, but soluble in aqueous media with a pH below 5, preferably a pH below 4. This functional coating is applied by conventional coating techniques, such as pan coating or fluid bed coating using solution, suspension or dispersion of polymeric material in water or suitable organic solvents.

The functional coating should comprise about 10 to 75 wt %, preferably about 15 to about 50 wt %, based upon the total dry weight of the functional coating, of a coating agent that is insoluble in water, but soluble in aqueous media with a pH below 5, preferably a pH below 4. The coating agent may be an amino methacrylate copolymer, preferably an aminoalkyl methacrylate copolymer. An example of a coating agent that is insoluble in water, but soluble in aqueous media with a pH below 5, preferably below 4, and most preferably below 3 is EUDRAGIT® E. Additional examples are EUDRAGIT® E 100, EUDRAGIT® E PO and EUDRAGIT® 12.5. EUDRAGIT® E 100 is a poly(butyl methacrylate, (2-dimethyl amino ethyl)methacrylate, methyl methacrylate) copolymer. EUDRAGIT® E PO, which is also commercially available from Evonik Industries, is a cationic copolymer derived from poly(butyl methacrylate, (2-dimethyl aminoethyl)methacrylate, methyl methacrylate) and is soluble in gastric acid and in pH's up to 5.0. One g of EUDRAGIT® E PO dissolves in 7 g methanol, ethanol, isopropyl alcohol, ethyl acetate, methylene chloride or 1 N hydrochloric acid to give clear to slightly cloudy solutions, and has a viscosity of approximately 3-6 mPa's. EUDRAGIT® E 12.5 is a commercially available coating solution containing EUDRAGIT® E 100 (12.5 w/wt %) in a mixture of isopropyl alcohol and acetone. The pH dependent nature of the EUDRAGIT® E polymers allows the tranexamic dosage form to limit the release of the active agent until it has been deposited in the low pH gastric environment of the stomach. This allows for minimal release of tranexamic acid in the mouth, thereby overcoming the bitter taste. Further, because the functional coating does not completely obstruct the release of the tranexamic acid during the dosage form's period in the stomach, a therapeutic release of the active is still provided to the patient's stomach and upper part of the gastrointestinal tract.

In one embodiment of the present invention, the functional coating comprises about 1 to about 10 wt % based on the total weight of the dosage form, preferably about 2 to about 6 wt % based upon the total weight of the dosage form.

In the preparation of the tablets of the invention, various conventional, well-known solvents may be used to prepare the tablets and apply the functional coating to the tablets of the invention. In addition, various diluents, excipients, lubricants dyes, pigments, dispersants etc., which are disclosed in *Remingtons' Pharmaceutical Sciences,* 2000 Edition, may be used to optimize the formulations of the invention.

The functional coating can also contain additional coating agents that rapidly dissolve or disperse in aqueous media. One embodiment of the present invention employs a rapidly water soluble film forming agent such as low molecular weights hydroxypropyl methylcellulose, low molecular weight polyvinyl pyrrolidone, low molecular weight polyvinyl alcohols or mixtures thereof. As used herein the term "rapidly water soluble" means films prepared from the material will dissolve or disperse within 10 minutes when placed in 900 ml of water. Some of the film forming agents useful for incorporation into the functional coating of the present invention are commercially available from Colorcon under the trade name OPADRY®, such as OPADRY® clear, OPADRY® white or OPADRY® yellow. The film former if incorporated into the functional coating of the present invention should comprise about 20% to about 80%, preferably about 45% to about 75% based upon the total dry weight of the functional coating.

The functional coating may also contain plasticizers. Plasticizers that may be used include any of those known to those skilled in the art, including but not limited to, acetyltributyl citrate, triacetin, acetylated monoglyceride, rape oil, olive oil, sesame oil, acetyltriethyl citrate, glycerin sorbitol, diethyloxalate, diethylmalate, diethylfumarate, dibutylsuccinate, diethylmalonate, dioctylphthalate, dibutylphthalate, dibutylsebacate, triethyl citrate, tributylcitrate, glyceroltributyrate, polyethylene glycol, propylene glycol and mixtures thereof. The amount of plasticizer employed in the functional coating can range from about 0.1 to about 20%, and most preferably from about 1 to about 10% based on the total dry weight of the functional coating.

The functional coating may also include an inert processing aid or an anti-sticking agent such as those selected from the group consisting of talc, colloidal silica dioxide, magnesium stearate, magnesium silicate, glyceryl monostearates, calcium stearate or steric acid. If an anti-sticking agent is employed in the functional coating, the amount employed should range from about 0.1 to about 30%, and most preferably about 1 to 10% based on the total dry weight of the functional coating.

One embodiment of the present invention requires the core to be a homogeneous or unitary core that is compressed into a mini tablet or tablet. The compressed core may be formed by mixing the core ingredients and directly compressing the mixture. The core may also be formed by preparing a wet or dry granulation of the ingredients and compressing the granules into the core structure.

In one embodiment, the core is formed by wet granulating the core ingredients with water, isopropyl alcohol, acetone, ethanol or the like. The wet granules are dried and sized then blended with addition ingredients, i.e., extra-granular excipients, such as binders, fillers, disintegrants, glidants, lubricants and mixtures thereof, and the blend is compressed into the homogeneous or unitary cores.

Embodiments of the present invention may comprise the ingredients as outlined in the following table:

| Ingredient | Preferred (wt %) | Most Preferred (wt %) |
|---|---|---|
| Compressed matrix core[1] | | |
| Tranexamic acid | 50-90% | 55-85% |
| Release controlling material | 2-20% | 3-15% |
| Binder | 0.1-10% | 1-5% |
| Filler | 5-50% | 10-30% |
| Glidant | 0.01-5% | 0.1-2% |
| Disintegrant | 0.1-10% | 0.5-5% |
| Lubricant | 0-10% | 0-5% |
| Functional coating[2] | | |
| Coating agent that is insoluble in water but soluble in aqueous media with a pH below 5 | 5-50% | 15-30% |
| Film former | 25-80% | 45-75% |
| Plasticizer | 0.1-20% | 1-10% |
| Anti-sticking agent | 1-30% | 5-15% |

[1]Wt % based on the total weight of the core.
[2]Wt % based on the total dry weight of the coating.

The dissolution profile of the dosage form prepared according to the present invention should exhibit the following dissolution profile when tested in a USP type 2 (paddle) apparatus at 50 rpms in 900 ml of water at 37° C.

| | DRUG RELEASED | |
|---|---|---|
| Time (minutes) | Preferred | Most Preferred |
| 15 | 0-20% | 0-10% |
| 30 | 0-40% | 10-20% |
| 45 | 5-50% | 10-30% |
| 60 | *NLT 10% | NLT 15% |
| 90 | NLT 15% | NLT 25% |
| 120 | NLT 25% | NLT 30% |
| 150 | NLT 30% | NLT 35% |

*NLT = Not Less Than

The dissolution profile of the dosage form prepared according to the present invention should exhibit the following dissolution profile when tested in a USP type 2 (paddle) apparatus at 50 rpms in 900 ml of 0.1 N HCl at 37° C.

| | DRUG RELEASED | |
|---|---|---|
| Time (minutes) | Preferred | Most Preferred |
| 15 | 10-50% | 25-45% |
| 30 | 40-95% | 60-85% |
| 45 | 50-99% | 80-99% |
| 60 | NLT 70% | NLT 80% |
| 90 | NLT 80% | NLT 95% |
| 120 | NLT 85% | NLT 90% |
| 150 | NLT 90% | NLT 95% |

EXAMPLES

The following are provided by way of example only and are in no means intended to be limiting.

Example 1

Granulation

The formulation for making the tranexamic acid granulation has the following composition:

| | |
|---|---|
| tranexamic acid, USP | 650.0 mg/tab |
| microcrystalline cellulose (AVICEL ® PH101) | 154.3 mg/tab |
| glyceryl behenate NF, (COMPRITOL ® 888 ATO) | 8.286 mg/tab |
| hypromellose, 2910 USP (METHOCEL ® E5 Premium) | 65.0 mg/tab |
| copovidone (PLASDONE ® S 630) | 27.86 mg/tab |

Copovidone is dissolved in a sufficient amount of ethanol to allow it to completely dissolve. Next, the tranexamic acid, microcrystalline cellulose, glyceryl behenate and hypromellose are passed through a comil and blended in a V-blender for approximately 15 minutes. The blend is then loaded into a high shear granulator and mixed for approximately 2 minutes. The solution of copovidone and ethanol is then sprayed onto the mixed blend in the granulator until the granulation is complete. The granulation is then dried in an oven at 60±5° C. until the loss on drying (LOD) is less than 1.2%. The dried granules are passed through a comil.

Blending

The comilled granulate is then blended with the following extra-granular ingredients:

| | |
|---|---|
| copovidone (PLASDONE S 630) | 4.741 mg/tab |
| crospovidone, NF (POLYPLASDONEe XL-10) | 19.49 mg/tab |
| lactose monohydrate, NF Modified Spray Dried (Lactose 316 Fastflo) | 24.42 mg/tab |
| colloidal silicon dioxide, NF (Cab-O-Sil M5P) | 4.741 mg/tab |
| magnesium stearate, NF | 9.481 mg/tab |

The copovidone, crospovidone, lactose monohydrate and colloidal silicon dioxide are passed through a comil. The comilled granules and comilled additional excipients are loaded into a V-blender and blended for approximately 15 minutes. Magnesium stearate is then screened through a 30 mesh screen and added into the V-blender with the blended mixture for approximately 5 minutes.

Tabletting

The blended granulation is tabletted into tablet cores containing 650 mg of tranexamic acid using a high speed rotary tablet press to form oval shaped tablets. The target weight is 968.6 mg/tab and the target hardness is 13-20 Kp.

Coating

A functional coating of the following formulation is then applied to the compressed tablet cores:

| | |
|---|---|
| tranexamic acid tablet cores (prepared above) | 968.3 mg/tab |
| OPADRY Clear*, YS-1-7006 | 18.54 mg/tab |
| EUDRAGIT ® E PO | 6.18 mg/tab |
| triethyl citrate, NF | 1.24 mg/tab |
| talc USP (Imperial Talc 500) | 3.09 mg/tab |

*OPADRY Clear is believed to contain hypromellose and polyethylene glycol

Triethyl citrate is added to acetone and isopropyl alcohol and allowed to homogenize. Next, talc is added to the solution and allowed to homogenize. A second solution is formed comprising acetone, isopropyl alcohol and purified water to which EUDRAGIT® E PO and OPADRY® Clear are sequentially dissolved. The two solutions are combined and stirred. The coating solution is then sprayed onto the compressed tablet cores until a total weight gain of 29.05 mg/tablet (3% weight gain) is achieved.

The resulting tablets were tested in two separate solutions containing water and simulated gastric fluid (SGF, pH 1.2, 0.1 N HCl), according to the procedure described in United States Pharmacopoeia 25, using Apparatus II, paddle @ 50 rpm in 900 ml. The mean results of three (3) in vitro tests were as follows:

In water:

| TIME (in minutes) | % RELEASED |
|---|---|
| 0 | 0 |
| 15 | 5 |
| 30 | 10 |
| 45 | 15 |
| 60 | 18 |
| 90 | 27 |
| 120 | 35 |
| 150 | 41 |

In SGF:

| TIME (in minutes) | % RELEASED |
|---|---|
| 0 | 0 |
| 15 | 37 |
| 30 | 73 |
| 45 | 94 |
| 60 | 97 |
| 90 | 97 |
| 120 | 97 |
| 150 | 98 |

The invention illustratively described herein suitably may be practiced in the absence of any element or elements, limitation or limitations, which is not specifically disclosed herein. Thus, for example, in each instance herein, any of the terms "comprising," "consisting essentially of" and "consisting of" may be replaced with either of the other two terms. The terms and expressions that have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:
1. A modified release dosage form comprising:
 (A) a compressed matrix core which comprises:
  (i) tranexamic acid;
  (ii) a release controlling material;
  (iii) a binder;
  (iv) a filler;
  (v) a glidant;
  (vi) a disintegrant; and
  (vii) optionally, one or more lubricants; and
 (B) a functional coating on said compressed matrix core which comprises
  (i) a coating agent which is insoluble in water but soluble in aqueous media with a pH below 4;
  (ii) a film former;
  (iii) a plasticizer; and
  (iv) an anti-sticking agent
 wherein the dosage form, exhibits the following dissolution profile when tested in a USP Type 2 (paddle) apparatus at 50 RPM in 900 ml of 0.1 N HCl at 37° C.: after 15 minutes 10-50% of the tranexamic acid is released; after 30 minutes 40-95% of the tranexamic acid is released; after 45 minutes 50-99% of the tranexamic acid is released; and after 60 minutes, not less than 70% of the tranexamic acid is released.
2. The modified release dosage form as defined in claim 1 where the filler is selected from the group consisting of sugars, lactose monohydrate, calcium phosphate, dextrin, dextrose, maltitol, maltose, starch, sucrose, or microcrystalline cellulose.
3. The modified release dosage form as defined in claim 1 wherein said filler comprises lactose monohydrate and microcrystalline cellulose.
4. The modified release dosage form as defined in claim 1 wherein the binder in the core is water soluble.

5. The modified release dosage form as defined in claim 1 where the binder in the core is selected from the group consisting of methyl cellulose, hydroxymethyl cellulose, polyvinyl pyrrolidone, hydroxyethyl cellulose, hydroxypropyl cellulose, hydroxypropyl methylcellulose, polyethylene oxides, gums, acrylate polymers, methacrylate polymers and copovidone.

6. The modified release dosage form as defined in claim 1 wherein the binder in the core is copovidone.

7. The modified release dosage form as defined in claim 1 where the glidant is selected from the group consisting of colloidal silicon dioxide and quso.

8. The modified release dosage form as defined in claim 1 wherein said glidant is colloidal silicon dioxide.

9. The modified release dosage form as defined in claim 1 where the disintegrant is selected from the group consisting of corn starch, potato starch, croscarmellose sodium, crospovidone and sodium starch glycolate.

10. The modified release dosage form as defined in claim 1 wherein said disintegrant is crospovidone.

11. The modified release dosage form as defined in claim 1 where the lubricant in the core is not optional and is selected from the group consisting of talc, glyceryl behenate, glyceryl monostearates, calcium stearate, magnesium stearate, stearic acid, and polyethylene glycol.

12. The modified release dosage form as defined in claim 1 wherein said lubricant in the core is glyceryl behenate.

13. The modified release dosage form as defined in claim 1 wherein the plasticizer is selected from the group consisting of acetyltributyl citrate, triacetin, acetylated monoglyceride, acetyltriethyl citrate, glycerin sorbitol, diethyloxalate, diethylmalate, diethylfumarate, dibutylsuccinate, diethylmalonate, dioctylphthalate, dibutylphthalate, dibutylsebacate, triethyl citrate, tributylcitrate, glyceroltributyrate, polyethylene glycol, propylene glycol and mixtures thereof.

14. The modified release dosage form as defined in claim 1 wherein the plasticizer is triethyl citrate.

15. The modified release dosage form as defined in claim 1 wherein the anti-sticking agent is selected from the group consisting of talc, colloidal silica dioxide, magnesium stearate, magnesium silicate, glyceryl monostearates, calcium stearate or steric acid.

16. The modified release dosage form as defined in claim 1 wherein the anti-sticking agent is talc.

17. The modified release dosage form as defined in claim 1 wherein the release controlling material is selected from the group consisting of gums, acrylic resins, waxes, polyethylene oxides, hydrogenated castor oil, hydrogenated vegetable oils, glycerol monostearate, glyceryl behenate, stearyl alcohol, alginates, carrageenan, carbomers, xanthan gum, locust bean gum, hydroxypropyl methylcelluloses, hydroxypropyl celluloses, hydroxyethyl celluloses, carboxymethycelluloses, and mixtures of thereof.

18. The modified release dosage form as defined in claim 1 wherein the release controlling material is a release controlling polymer.

19. The modified release dosage form as defined in claim 18 wherein the release controlling polymer is hydroxypropyl methylcellulose.

20. The modified release dosage form as defined in claim 1 wherein the coating agent which is insoluble in water but soluble in aqueous media with a pH below 4 is selected from the group consisting of amino methacrylate copolymers.

21. The modified release dosage form as defined in claim 1 wherein the coating agent which is insoluble in water but soluble in aqueous media with a pH below 4 is an aminoalkyl methacrylate copolymer.

22. The modified release dosage form as defined in claim 1 wherein the film former is a rapidly water soluble film forming agent.

23. A modified release dosage form consisting essentially of:
 (A) a compressed matrix core which comprises:
  (i) 50-90 weight percent of tranexamic acid;
  (ii) 2-20 weight percent of a release controlling material;
  (iii) 0.1-10 weight percent of a binder;
  (iv) 5-50 weight percent of a filler;
  (v) 0.01-5 weight percent of a glidant;
  (vi) 0.1-10 weight percent of a disintegrant; and
  (vii) optionally, 0-10 weight percent of one or more lubricants; and
 (B) a functional coating on said compressed matrix core which comprises:
  (i) 5-50 weight percent based upon the total weight of the functional coating of a coating agent which is insoluble in water but soluble in aqueous media with a pH below 4;
  (ii) 25-80 weight percent based upon the total weight of the functional coating of a film former;
  (iii) 0.1-20 weight percent based upon the total weight of the functional coating of a plasticizer; and
  (iv) 1-30 weight percent based upon the total weight of the functional coating of an anti-sticking agent
 wherein the dosage form, exhibits the following dissolution profile when tested in a USP Type 2 (paddle) apparatus at 50 RPM in 900 ml of 0.1 N HCl at 37° C.: after 15 minutes 10-50% of the tranexamic acid is released; after 30 minutes 40-95% of the tranexamic acid is released; after 45 minutes 50-99% of the tranexamic acid is released; and after 60 minutes, not less than 70% of the tranexamic acid is released.

24. The modified release dosage form as defined in claim 23 consisting essentially of:
 (A) a compressed matrix core which comprises:
  (i) 55-85 weight percent of tranexamic acid;
  (ii) 3-15 weight percent of a release controlling material;
  (iii) 1-5 weight percent of a binder;
  (iv) 10-30 weight percent of a filler;
  (v) 0.1-2 weight percent of a glidant;
  (vi) 0.5-5 weight percent of a disintegrant; and
  (vii) optionally, 0-5 weight percent of one or more lubricants; and
 (B) a functional coating on said compressed matrix core which comprises:
  (i) 15-30 weight percent based upon the total weight of the functional coating of a coating agent which is insoluble in water but soluble in aqueous media with a pH below 4;
  (ii) 45-75 weight percent based upon the total weight of the functional coating of a film former;
  (iii) 1-10 weight percent based upon the total weight of the functional coating of a plasticizer; and
  (iv) 5-15 weight percent based upon the total weight of the functional coating of an anti-sticking agent
 wherein the dosage form, exhibits the following dissolution profile when tested in a USP Type 2 (paddle) apparatus at 50 RPM in 900 ml of 0.1 N HCl at 37° C.: after 15 minutes 10-50% of the tranexamic acid is released; after 30 minutes 40-95% of the tranexamic acid is released; after 45 minutes 50-99% of the tranexamic acid is released; and after 60 minutes, not less than 70% of the tranexamic acid is released.

* * * * *